US00PP31648P2

(12) United States Plant Patent
Wheeler et al.

(10) Patent No.: US PP31,648 P2
(45) Date of Patent: Apr. 14, 2020

(54) BLUEBERRY PLANT NAMED 'BB06-126VC-4'

(50) Latin Name: *Vaccinium corymbosum*
Varietal Denomination: BB06-126VC-4

(71) Applicant: Berry Blue, LLC, Grand Junction, MI (US)

(72) Inventors: Edmund J. Wheeler, Holland, MI (US); James F. Hancock, Scarborough, ME (US); Maria Pilar Banados, Santiago (CL)

(73) Assignee: Berry Blue, LLC, Grand Junction, MI (US)

( * ) Notice: Subject to any disclaimer, the term of this patent is extended or adjusted under 35 U.S.C. 154(b) by 0 days.

(21) Appl. No.: 16/350,418

(22) Filed: Nov. 13, 2018

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368
See application file for complete search history.

*Primary Examiner* — Anne Marie Grunberg
(74) *Attorney, Agent, or Firm* — King IP Law; Joshua King

(57) ABSTRACT

'BB06-126VC-4' is a new and distinct medium-chill southern highbush blueberry variety of plant. 'BB06-126VC-4' is a productive early ripening variety which provides a very good yield potential with very good plant vigor, fruit quality, flavor, crunchy texture, and high firmness. 'BB06-126VC-4' is suitable for areas that successfully grow lower chill Southern highbush varieties. The fruit of 'BB06-126VC-4' are very large, typically 18 mm or more in diameter with an average berry weight of 2.9 gram per berry, well exposed on a medium upright bush with a small crown. 'BB06-126VC-4' has very good flavor with a balanced amount of sugar and acidity and is also very firm and juicy.

5 Drawing Sheets

Latin name of the genus and species of the plant claimed: *Vaccinium corymbosum.*

Variety denomination: BLUEBERRY PLANT NAMED 'BB06-126VC-4'.

BACKGROUND AND SUMMARY

Blueberries are a well-known fruit enjoyed by many throughout the world. One example of an existing commercial blueberry variety is 'Duke', unpatented. Another example of an existing, patented blueberry variety is 'Emerald', U.S. Plant Pat. No. 12,165.

Comparing 'BB06-126VC-4' to 'Duke', the immature summer cane color of 'BB06-126VC-4' is olive green compared to red for 'Duke'; the fruit of 'BB06-126VC-4' is appreciably larger in size and more rounded than 'Duke'.

Comparing 'BB06-126VC-4' to 'Emerald', 'BB06-126VC-4' ripens about 7 days later and has a more concentrated ripening season than 'Emerald'; the bush shape of 'BB06-126VC-4' is more vigorous and upright than 'Emerald'; 'BB06-126VC-4' has fewer but more vigorous upright capes compared to 'Emerald'.

The present cultivar, 'BB06-126VC-4', provides one or more advantages compared to these and/or other blueberry varieties.

BRIEF DESCRIPTION THE PHOTOGRAPHS

DETAILED DESCRIPTION

Figure 1:
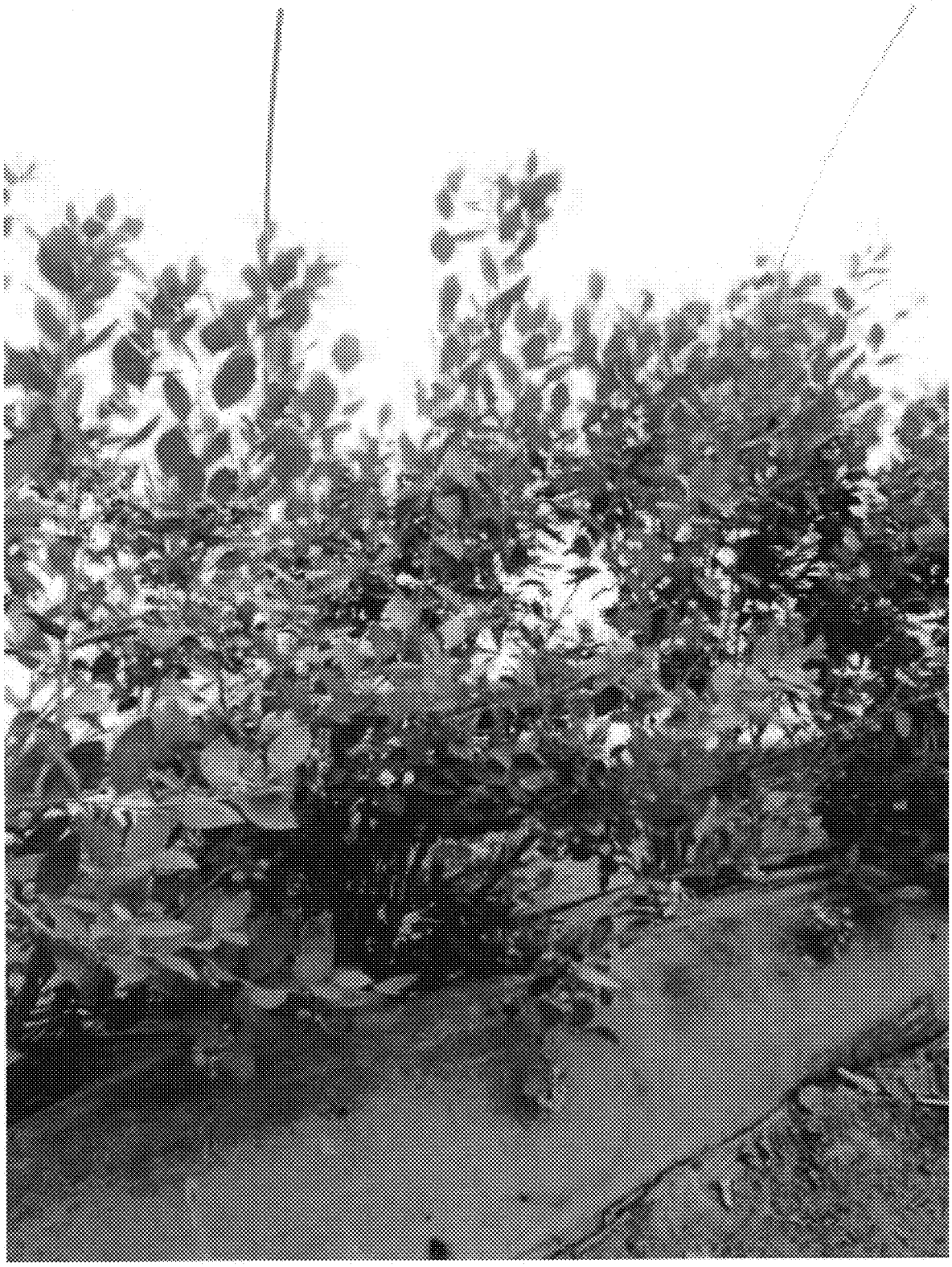
FIG. 1 is a photograph of 3-year-old plants of 'BB06-126VC-4' in Nancagua, Chile, November 2017, showing the bush habit, foliage color and form, cane structure, summer color of the canes, immature fruit, fruit presentation and fruit cluster density.
Figure 2:
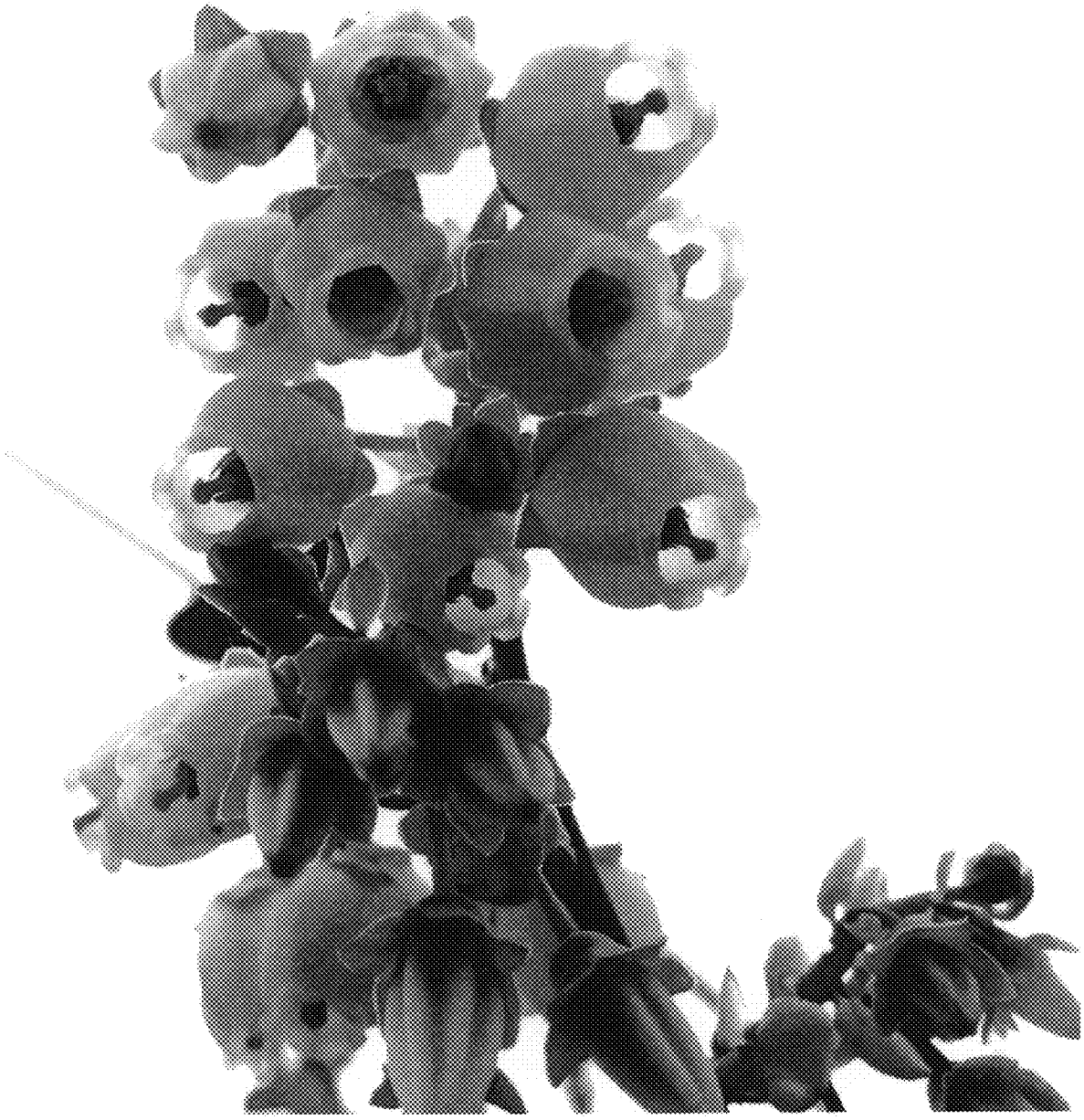
FIG. 2 is a second close-up photograph of 'BB06-126VC-4' in Nancagua, Chile, September 2017, showing the winter cane color, the color and shape of opened and un-opened flowers and the color of the peduncle and pedicel.
Figure 3:
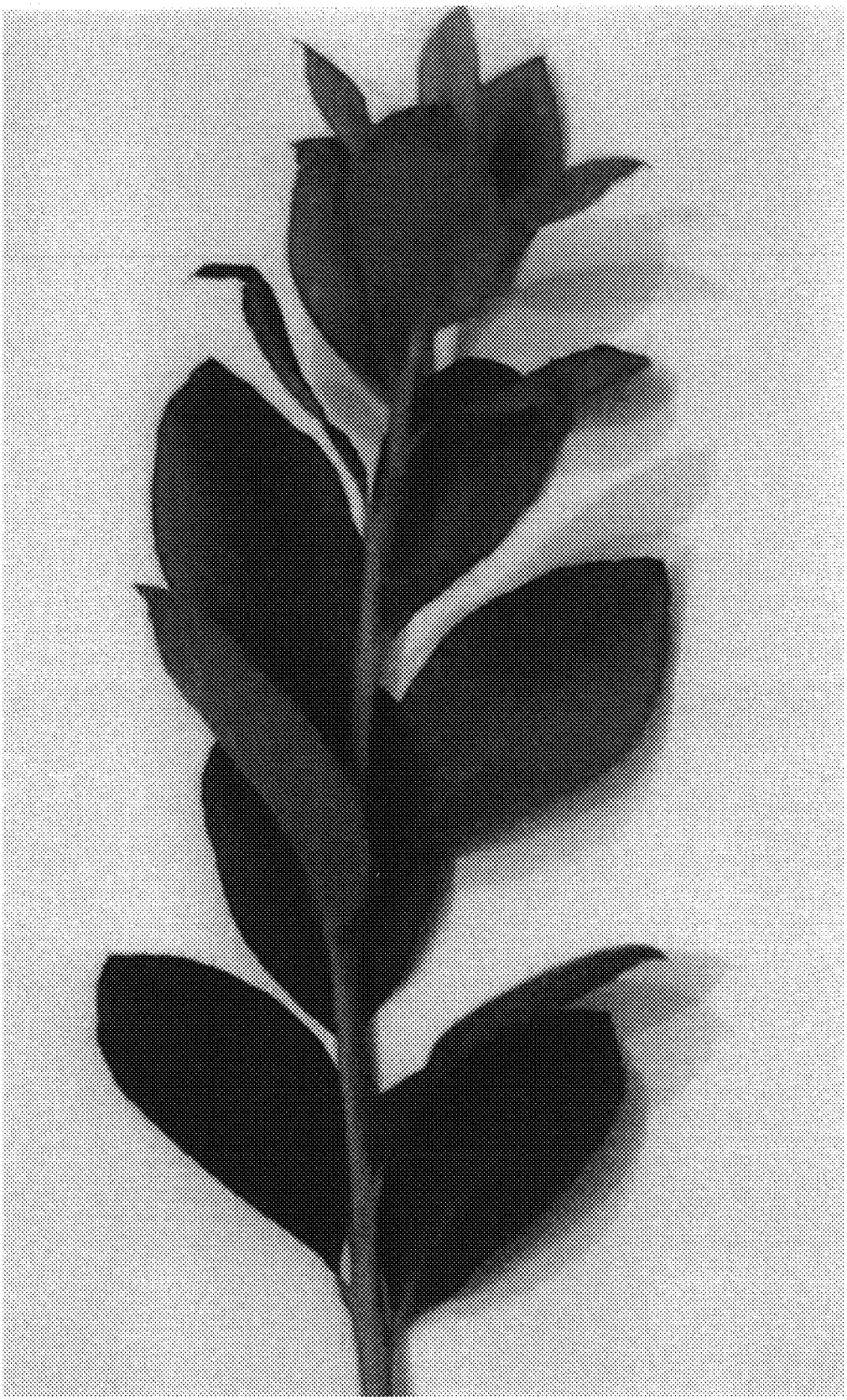
FIG. 3 is a close-up photograph of a one-year old cane of 'BB06-126VC-4', in Nancagua, Chile, December 2017, showing the leaf color and shape, summer cane color and the arrangement of the leaves on a shoot.
Figure 4:
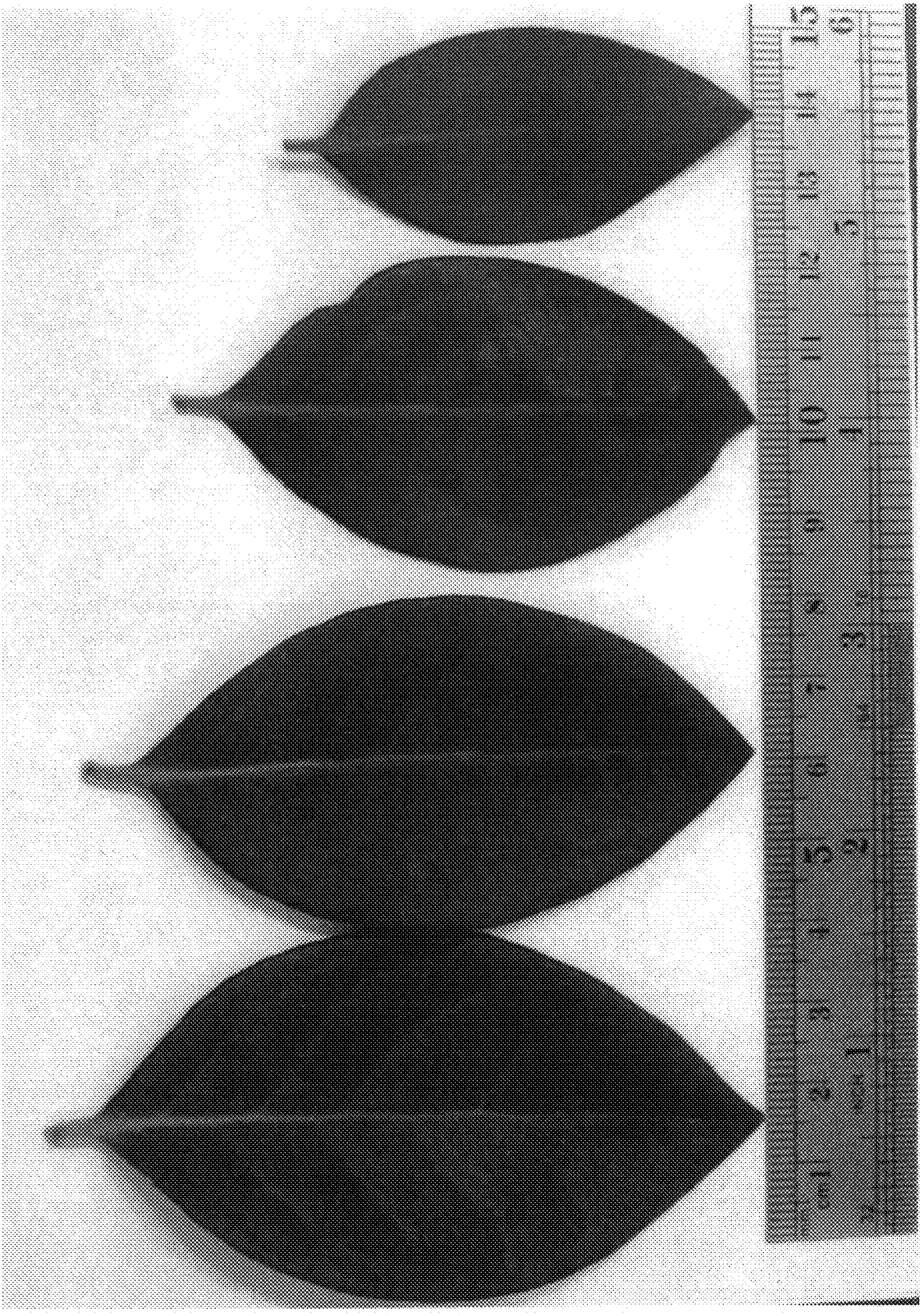
FIG. 4 is a close-up photograph of mature leaves of 'BB06-126VC-4' in Nancagua, Chile, December, 2017, showing the shape, color, leaf base and apice shapes, leaf venation and petiole length and color.
Figure 5:
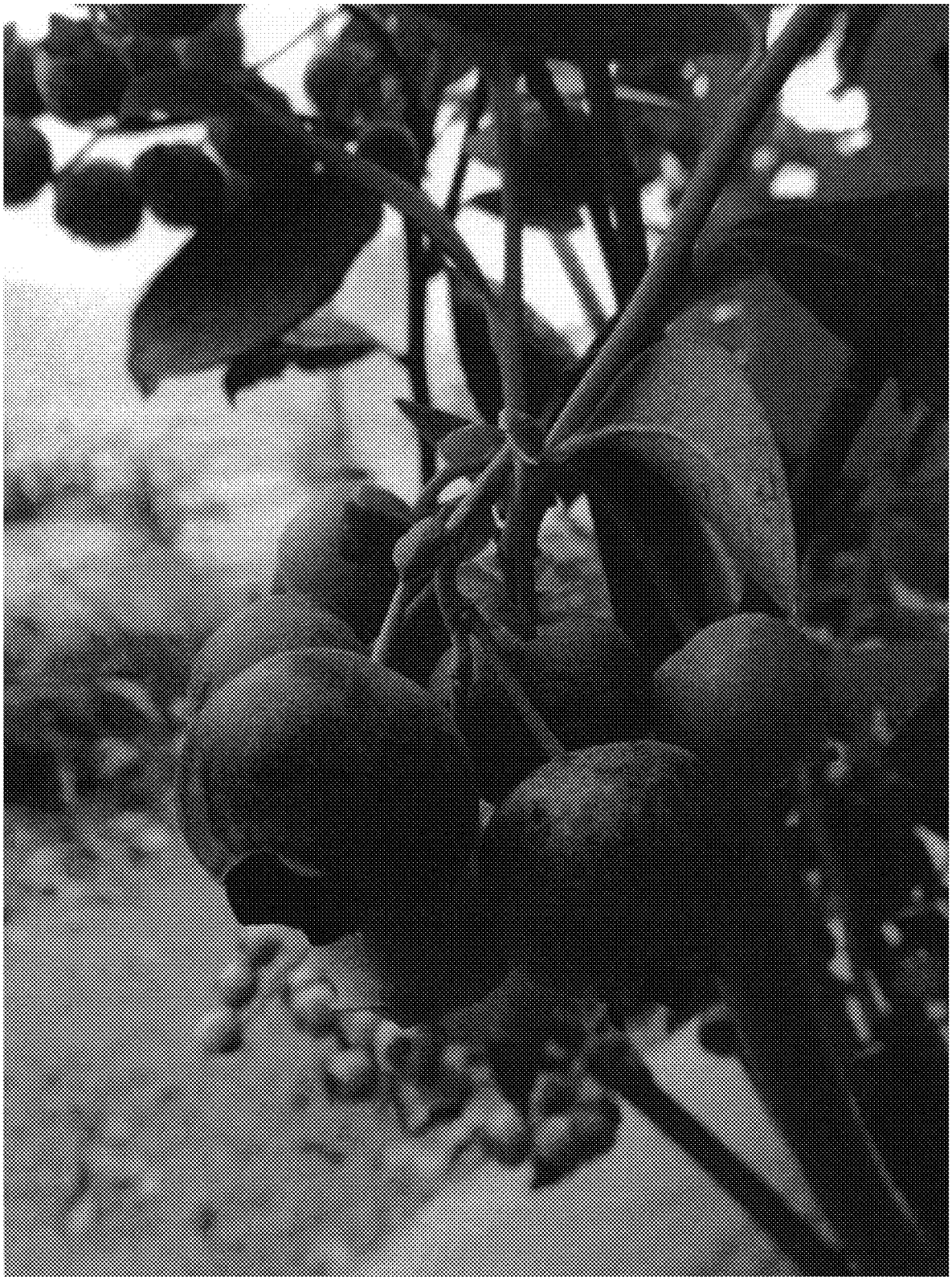
FIG. 5 is a close-up photograph of the ripe and immature fruit of 'BB06-126VC-4', in Nancagua, Chile, December 2017, showing their shape, color and amount of waxy bloom, the pedicel length and color, the fruit cluster density, summer cane color, mature leaves and their shape and color.

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are largely based on 5 bush replications in advanced trials located near Nancagua, Chile and Los Angeles, Chile. Laboratory analysis of fruit characteristics were done in Santiago, Chile. The bushes in the advanced trials were propagated from the original mother bush selected near Los Angeles, Chile and have retained the characteristics of the original selection.

Cultivar Name: 'BB06-126VC-4'.

Classification:

Family: Ericaceae.

Botanical name: *Vaccinium corymbosum.*

Common name: Blueberry.

Parentage:

Female Parent

Name: 'Camellia'

U.S. Plant Pat. No. 18,151

Compared to Camellia, for 'BB06-126VC-4' the date of 50% ripening is 10 to 12 days earlier in Nancagua, Chile. 'BB06-126VC-4' has a much larger and firmer fruit than 'Camellia'. The fruit firmness and the postharvest life for 'BB06-126VC-4' is much higher than for 'Camellia'. Plant productivity is moderate; in a field in Nancagua, Chile at 3 years old the average yield per plant was 2.8 Kg.

Male Parent

Name: 'Rebel'

U.S. Plant Pat. No. 18,138.

Compared to 'Rebel', 'BB06-126VC-4' is larger in size, firmer and has a darker blue color. Plant vigor for 'BB06-126VC-4' is higher than for 'Rebel'. The flavor of 'BB06-126VC-4' is more intense than 'Rebel', although both are low acid varieties.

'BB06-126VC-4' originated from the cross of 'Camellia' x 'Rebel' made in a greenhouse in Grand Junction, Mich. in 2006. Seeds of this cross were collected, sent to Chile, were germinated, and grown as seedlings near Hijuelas, Chile. The seedlings were grown for a period of 15 months and then planted in an observational trial site in Los Angeles, Chile (37° 27'84'S; 72° 30'70'W) in spring 2009. 'BB06-126VC-4' was selected in December 2011 for its interesting morphological characteristics of large firm fruit and a vigorous plant. During the summer (February) of 2012, 'BB06-126VC-4' was asexually propagated by tissue culture in Hijuelas, Chile, and in November 2013 was planted in a multi-bush advanced selection trials in Nancagua, Chile (34° 43'58'S; 71° 10'21'W). As a part of this process, actively growing nodal vegetative but explants were harvested from greenhouse potted stock, sterilized, and placed in culture vessels with WPM medium (see, Commercially-feasible micropropagation of Mountain Laurel, *Kalmia latifolia*, by shoot tip culture. Lloyd, G., and McCown, B. H. Proc. Int. Plant Prop. Soc. 30, 421-427, (1981)) supplemented with agar/gelrite and 5 μM Zeatin. Cultures were grown under 20 hours of LED white light at 20° to 24° C. After multiple subcultures to generate shoot cultures, 2 to 4 cm microcuttings were rooted and acclimated under in a peat/perlite rooting mix under high humidity. The evaluations of 'BB06-126VC-4' were made in each of years 2014, 2015, 2016 and 2017 both under plastic tunnel and open field cultures. 'BB06-126VC-4' was also planted in Los Angeles, Chile in a multi-bush advanced trial in May 2015, and fruit of this planting was evaluated for the first time in 2016. All propagated plants have retained the original characteristics.

'BB06-126VC-4' is a new and distinct medium-chill highbush blueberry variety. 'BB06-126VC-4' is a productive early ripening variety. 'BB06-126VC-4' provides a very good yield potential, very good plant vigor, fruit quality, flavor, texture, and firmness.

Botanical/classification: *Vaccinium corymbosum* interspecific hybrid

The desirable features of 'BB06-126VC-4' include a combination of attributes that are outstanding in a new variety, including for example:

1. Early-midseason ripening.
2. High yields of very large sized fruit.
3. Very good fruit quality, excellent fruit firmness.
4. Fruit with a long post-harvest life of excellent quality.

'BB06-126VC-4' flowers and produces fruit and appears to be well adapted for areas having between 500 to 750 chilling hours below 7° C. (counted from May 1$^{st}$ to July 31$^{st}$ in the temperate zone of Chile, southern hemisphere where it was selected and tested). It produces early to mid-season ripe fruit. 'BB06-126VC-4' is a highly vigorous plant, semi-erect with high yield potential if managed well. Fruit is very large, of round shape, very firm, medium dark blue in color, with a small pedicel scar, and low acid flavor. Blueberry flavor is only moderate at harvest time and it can be intensified in cold (0° C.) storage. 73% of the total harvested fruit is very large in size, greater than 18 mm.

References to color refer to R.H.S Colour Chart, by Royal Horticultural Society, 2007, 5$^{th}$ Edition, London.

Morphological characteristics reference: Plant Systematics, Jones and Usinger, 2 Ed., McGraw Hill, New York, ISBN 0-07-032796-3, 1986.

Fruit firmness measurements: Baxlo Precision, Pso.Sanllehy, Bloque 6, Nave 2—Polígono Industrial SUDESTE, 08213 POLINYÀ (Barcelona)—Spain.

Device used to measure Soluble Solids (SS-Brix°), Titratable acidity (TA), pH: PAL-BX/Acid 7, Atago USA, Inc., Bellevue, Wash.

Average size information:

*Growth.*—1.5 Meters height×1 meter width, semi-erect habit.

*Productivity.*—2.8 kilograms per plant in the 3$^{rd}$ year (Nancagua, Chile).

*Cold hardiness.*—−5° C. flower buds, −2° C. fruit.

Specific features of the variety:

Plant:

*Growth habit.*—Semi-erect.

*Plant width.*—1 meter.

*Plant height.*—1.5 meters.

*Productivity.*—2.8 kilograms per plant at the 3$^{rd}$ year.

*Cold hardiness/tolerance.*—−5° C. flower buds and flowers, −2° C. fruit.

*Chilling requirement.*—Estimated 500 to 650 hours between 0° to 7° C. counted between May to July in the Nancagua, Chile area.

*Canes.*—Moderately branched, average 6 to 7 canes per plant, average 65 cm in length, medium number of laterals.

*Mature cane color.*—Light Brown (165C).

*Texture.*—Rough

*Fruiting wood.*—Medium Green (145A).

*Internode length range.*—2.5 cm.

*Surface texture of new wood.*—Smooth.

*Time of beginning of leaf bud burst.*—Early to mid-August, Los Angeles, Chile.

*Time of beginning of flowering.*—Early September, Los Angeles, Chile.

*Time of fruit ripening.*—Mid-November through mid-December, Los Angeles, Chile.

*Disease resistance/susceptibility.*—None claimed.

Foliage:
*Leaf color*.—Medium Green (137B).
*Leaf arrangement*.—Alternate.
*Leaf margins*.—Entire.
*Leaf venation*.—Pinnate.
*Leaf apices*.—Acute.
*Leaf bases*.—Acute.
*Vein and petiole coloration*.—Medium Green (145A).
*Petiole length*.—6 mm.

Leaf dimensions:
*Overall shape*.—Elliptic.
*Length*.—7.5-9 cm range.
*Width*.—4 cm.
*Leaf apices*.—Acute.
*Leaf bases*.—Acute.
*Leaf margins*.—Entire.
*Leaf venation*.—Pinnate.
*Leaf surface upper and lower*.—Smooth.
*Petiole length*.—6 mm.
*Vein and petiole coloration*.—Medium Green (145A).
No visible nectaries or pubescence.

Leaf buds:
*Shape*.—Medium obtuse.
*Length*.—2.5 mm.
*Width*.—1.5 mm.
*Color*.—Medium Green (145A).

Flower:
*Flower shape*.—Urceolate.
*Flower bud number*.—10-12.
*Flowers per cluster*.—10-12 flowers per cluster.
*Flower fragrance*.—Herbal.
*Corolla color*.—White (155D).
*Corolla length*.—1 cm.
*Corolla aperture width*.—5 mm.
*Flower peduncle*.—6 mm.
*Flower peduncle diameter*.—1 mm.
*Flower peduncle texture*.—Smooth.
*Flower peduncle color*.—Medium Green (145A).
*Flower pedicel*.—3 mm.
*Flower pedicel diameter*.—1.5 mm.
*Flower pedicel texture*.—Smooth.
*Flower pedicel color*.—Medium Green (145A).
*Calyx* (*with sepals*).—3 mm.
*Calyx color*.—Medium Green (145A).

Stamen:
*Length*.—4 mm.
*Number per flower*.—10.
*Filament color*.—Medium Orange (22A).
*Anther length*.—5 mm.

Pistil:
*Length*.—9 mm, even with top of the corolla.
*Pistil color*.—Medium Green (145A).
*Ovary color*.—Medium Green (145A).
*Number*.—1 per flower.

Pollen:
*Abundance*.—High.
*Color*.—Yellow (10D).

Fruit:
*Date of 50% maturity*.—Early December in Los Angeles, Chile.
*Duration of ripening*.—Three and a half weeks from mid-December through early January in Los Angeles, Chile.
*Yield*.—2.8 kilograms per plant in the 3$^{rd}$ year after planting.
*Immature fruit color*.—Light Green (142D).
*Berry color with wax*.—Violet-Blue (98C).
*Berry color with wax removed*.—Black (202A).
*Berry flesh color*.—Yellow-Green (149D).
*Berry surface wax abundance*.—Sparse to medium.
*Berry weight*.—2.6 to 4 grams per berry, average 2.9 grams.
*Berry size*.—Very large (18 mm).
*Berry shape*.—Oblate.
*Cluster density*.—Loose.
*Average number of berries per cluster*.—9-12.
*Average weight of fruit per cluster*.—32 grams.
*Detachment force*.—Easy.
*Self-fruitfulness*.—Fair, will need cross pollination for maximum size and yield.
*Fruit stem scar*.—2 mm diameter, 1 mm depth
*Calyx*.—5 lobed.
*Calyx diameter*.—7 mm.
*Calyx depth*.—1.5 mm.
*Berry firmness*.—85 Shore.
*Berry sweetness* (*ss*).—12.3 Brix°.
*Titratable acidity* (*ta*).—0.25% to 0.4% acidity.
*Berry flavor and texture*.—Flavor is mild and not very intense, crunchy.
*Storage quality*.—Long postharvest life, it can be stored at 0° C. up to 40 days.
*Suitability for mechanical harvesting*.—Not tested.
*Uses*.—Fresh Market.

Seed:
*Seed abundance in fruit*.—30-50 per fruit.
*Seed color*.—Medium Brown (165B).
*Seed dry weight*.—NA.
*Seed size*.—1 mm width×1.5 mm length.

Possible typical market uses: Fresh market.

What is claimed is:

1. A new and distinct cultivar of Blueberry plant named 'BB06-126VC-4' as described and shown herein.

* * * * *